United States Patent
Yokote

(10) Patent No.: US 7,399,983 B2
(45) Date of Patent: Jul. 15, 2008

(54) QUALITY INSPECTION METHOD AND QUALITY INSPECTION DEVICE

(75) Inventor: Ryuji Yokote, Tokyo (JP)

(73) Assignee: Tetra Laval Holdings & Finance S.A., Pully (CH)

( * ) Notice: Subject to any disclaimer, the term of this patent is extended or adjusted under 35 U.S.C. 154(b) by 290 days.

(21) Appl. No.: 10/531,253

(22) PCT Filed: Oct. 8, 2003

(86) PCT No.: PCT/JP03/12860

§ 371 (c)(1),
(2), (4) Date: Mar. 28, 2006

(87) PCT Pub. No.: WO2004/036200

PCT Pub. Date: Apr. 29, 2004

(65) Prior Publication Data

US 2006/0175560 A1    Aug. 10, 2006

(30) Foreign Application Priority Data

Oct. 15, 2002   (JP) ............................... 2002-300323

(51) Int. Cl.
*G01D 5/36* (2006.01)
(52) U.S. Cl. .............................. 250/559.4; 250/559.39; 382/142; 382/143
(58) Field of Classification Search ........................ 250/559.01–559.44; 348/142, 143
See application file for complete search history.

(56) References Cited

U.S. PATENT DOCUMENTS

| | | | | |
|---|---|---|---|---|
| 6,806,459 B1 * | 10/2004 | Ringlien et al. ......... | 250/223 B |
| 7,167,803 B2 * | 1/2007 | Kinoshita et al. ............ | 702/35 |
| 7,230,229 B2 * | 6/2007 | Gerard et al. ............ | 250/223 B |
| 2006/0026929 A1 * | 2/2006 | Kinoshita et al. ............ | 53/551 |
| 2006/0175560 A1 * | 8/2006 | Yokote ................... | 250/559.45 |
| 2006/0255110 A1 * | 11/2006 | Kaneko ................. | 229/125.14 |

FOREIGN PATENT DOCUMENTS

| JP | 59-154641 U1 | 10/1984 |
|---|---|---|
| JP | 7-4954 A | 1/1995 |
| JP | 7-146251 A | 6/1995 |
| JP | 9-207921 A | 8/1997 |

* cited by examiner

Primary Examiner—Georgia Y. Epps
Assistant Examiner—Tony Ko
(74) Attorney, Agent, or Firm—Buchanan Ingersoll & Rooney PC

(57) ABSTRACT

In an inspection for protrusion of the melted thermoplastic material of transversal line seal into inside, it is an object to provide a quality inspection method and a quality inspection device which can easily detect projection on edge of seal, securely capture even fine unevenness which could not visually found, and allows for accurate and reliable inspection without variation of inspection.

The quality inspection method comprise steps of returning container formed from a web-like packaging laminated material to a shape of pillow-like preliminary forming, cutting container wall to sample a filled food, preparing the sampled body, measuring an edge of the transversal seal zone on the inside of the container over the whole length of the outer surface of the edge for unevenness of the outer surface by a detecting unit, and judging an acceptability of the transversal seal zone based on signals from the detecting unit by an analyzing unit.

6 Claims, 8 Drawing Sheets

(a)

(b)

QUALITY INSPECTION METHOD AND QUALITY INSPECTION DEVICE

TECHNICAL FIELD

This invention relates to an inspection method and an inspection device for inspecting quality of paper-made container and the like filled with liquid foods such as a juice and a milk.

TECHNICAL BACKGROUND

A finally shaped paper-made container filled with liquid foods such as a juice and a milk is obtained by forming a web-like packaging laminated material having a predetermined folding line in tubular shape, longitudinally sealing in the longitudinal direction of the tube, filling foods into the tubular packaging material, pressing the tubular packaging material in the predetermined intervals to seal the same by transversal seal in transversal direction, cutting at the center of the transversal seal zone to obtain a pillow-like preliminary forming, and sealing the flap containing the transversal seal zone formed by folding along the folding line on the side wall of the container and bottom face of the container.

FIG. 1 shows an outline of one example of a filling packaging machine for the paper-made container. The filling machine shown in this example winds out a packaging material web 1 having thermoplastic material layer on the inner and outer layers, wound in roll shape, and transfers it in the filling machine by rollers. A strip tape 2 is bonded to one end of the packaging material web by a strip tape applicator 3. The packaging material web is sterilized by passing through a sterilizing bath 4. Sterilizing agents are removed by an air knife 5. The tubular packaging material is formed by a forming roller 6. An overlap is formed by lapping both ends of the packaging material. The overlap is longitudinally sealed in the tube longitudinal direction by a longitudinal seal element 8. Liquid food is filled into the tube from a filling pipe 7. This tube, while being sent downward by a length equivalent to one packaging container, is sandwiched by a sealing jaw 10 and an oppositely arranged jaw 11. Two transversal seal zones are formed by the transversal seal in the crossing direction. A pillow-like preliminary forming 12 is continuously formed. The middle of the seal zone of the connected pillow-like preliminary forming is cut by knife or the like, and the forming is separated to individual pillow-like preliminary forming 13. A finally shaped packaging filling container 14 by folding flaps on the upper and lower of the separated pillow-like preliminary forming at a final folder 15.

FIG. 2 shows a feature in which the pillow-like preliminary forming 13 is folded at the final folder 15. The pillow-like preliminary forming 13 is sealed by two transversal (transversal line) seal zone 23 and longitudinal seal zone 26. The pillow-like preliminary forming 13 has side walls 22, 22b and 22a defined by the folding lines (refer to FIG. 2(a)).

As shown in FIG. 2(b), the main body of the pillow-like preliminary forming is formed in rectangular solid along folding lines. On the edge, the transversal seal zone 23 and flaps 24, 25 are formed to be upright from the container wall. The transversal seal zone 23 is upright from the bottom face 22b and the top face 22a. The flaps 24 and 25 integrally communicate with the container wall through ridge sides 25a and 24a.

Next, as shown in FIG. 2(c), after the transversal seal zone 23 is folded, the flaps are rotated around the ridge side as a center. A container top side flap 24 folded into the side wall 22, and the container bottom side flap 25 is folded into the bottom face 22b.

FIG. 3 shows a perspective view of outline of rectangular solid liquid food filling paper-made container. The container 14 has the transversal seal zone 23 and longitudinal 26 running to the bottom face from the container walls 22 and 22a and the top wall 22a through the container wall on the back. The folded flap 24 is provided through the ridge side 24a.

Sufficient sealing must be carried out at the above-mentioned seal zone so as to prevent the liquid food contained in the container from leaking and being exposed to external air. However, if the temperature and pressure on the transversal seal are improper, the melted thermoplastic material on the packaging laminated material may protrude into the container in which the content is filled. The melted substance directly contacts the contained liquid foods, and becomes brittle by sharply cooling, and the laminated material may be broken from the protruded location. For sealing, it is necessary to obtain a transversal seal whose melted substance does not protrude into the container.

Then, liquid food containers made by the filling packaging machine are regularly sampled by the operator of the machine for inspection. For the sampled container, the flap is peeled from the container wall so as to change the rectangular solid container to pillow-shaped by a substantially reverse method of the container final shape forming, that is, a method reverse to the method in which the flap is folded by the final folder of the filling packaging machine.

The transversal seal is inspected by visually measuring the seal strength, and presence or absence of pinhole, in addition, an edge on the inside of the container on the transversal seal zone for unevenness on the outer surface over the whole length of the outer surface of the edge.

In the conventional edge appearance inspection of the transversal seal, for the containers regularly sampled by the operator, the appearance on the inside of the edge of the transversal seal is visually observed, and then presence or absence of thermoplastic resin such as polyethylene protruded from the transversal seal zone is checked. Because the projection is transparent, it is not easy to find it and it is difficult to securely capture fine uneven defects.

There occur some variations in inspection due to individual difference in operator in the inspection for inspecting a melted thermoplastic material of the transversal line seal protrusion into inside, thereby reliability of the inspection is getting lower, and then more accurate and reliable inspection is required.

DISCLOSURE OF THE INVENTION

This invention is intended to provide a quality inspection method and quality inspection device for easily detecting projection on seal edge in inspection for protrusion of a melting thermoplastic material of transversal line seal into inside. This invention is also intended to provide a method and device capable of securely capturing even fine uneven defects which cannot be visually captured. This invention is further intended to provide a quality inspection method and quality inspection device allowing for accurate and reliable inspection without variation in inspection.

A quality inspection method and quality inspection device according to this invention is a quality inspection method for finally shaped container obtained by forming a web-like packaging laminated material having folding lines in tube shape, longitudinally sealing the packaging material in the longitudinal direction, filling food into the tube-shaped packaging material, pressing the packaging material at every predetermined interval in the crossing direction to seal by the transversal seal, cutting at the middle of the transversal seal zone to obtain a pillow-like preliminary forming, and sealing a flap formed by folding along the folding line to the container side wall and/or a container bottom face, comprising:

rotating the flap sealed to the container wall around a ridge side in which the flap integrally communicates with the container wall to peel the flap from the container wall;

returning to a shape of the pillow-like preliminary forming;

cutting the container wall to extract the filled food;

developing the cut container to prepare the sampled body;

measuring an edge of the transversal seal zone on the inside of the container over the whole length of the outer surface of the edge for unevenness of the outer surface by a detecting unit; and judging acceptability of the transversal seal zone based on signals from the detecting unit by an analyzing unit.

This allows projection on edge of the seal to be easily detected in the inspection for protrusion of a melting thermoplastic material of transversal line seal into inside. Fine uneven defects which could not be visually found can be securely captured. Accurate and reliable inspection without variation in inspection is allowed.

BEST MODE FOR CARRYING OUT THE INVENTION

Figure 1:
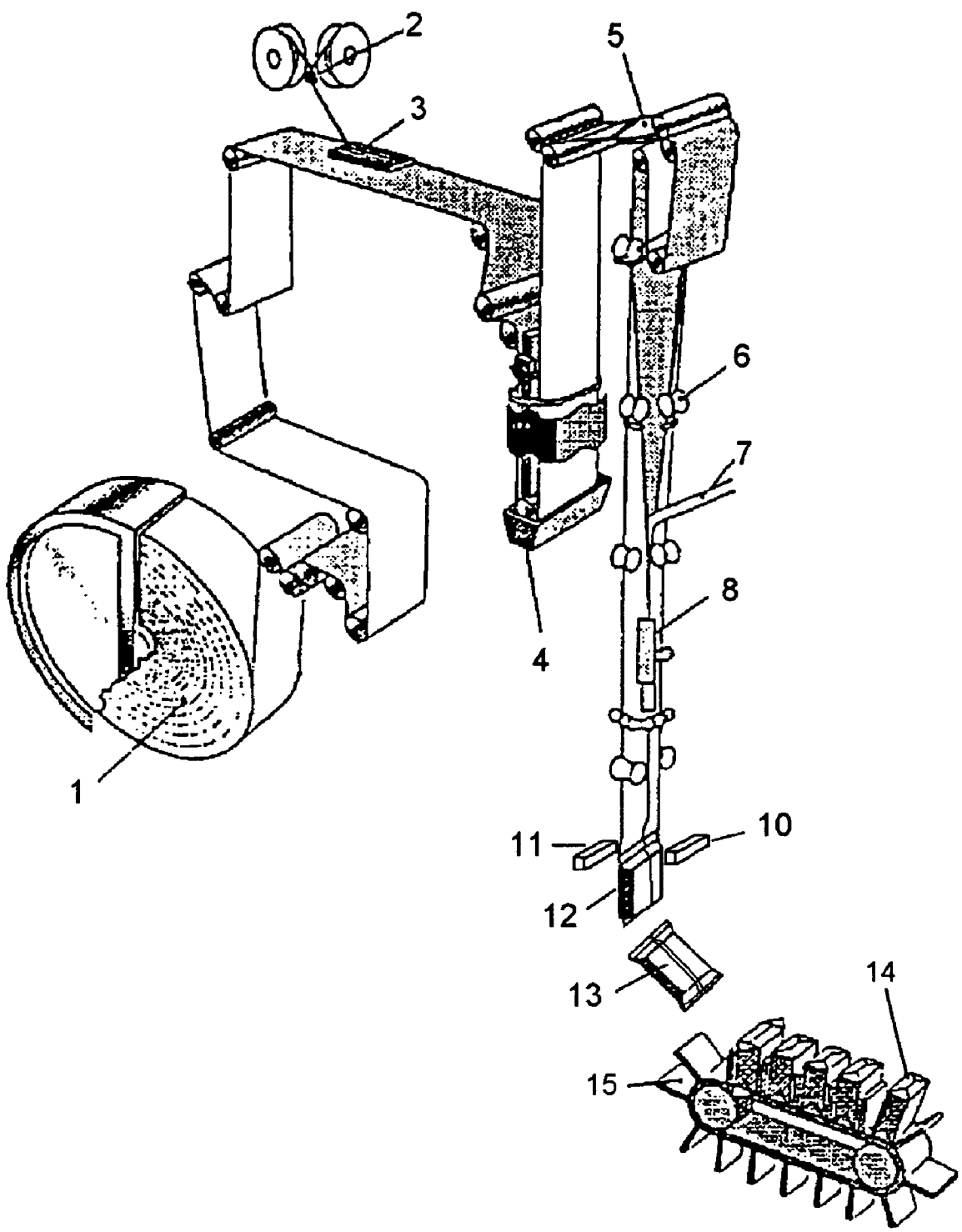
FIG. 1 is an overview of a packaging filling machine for paper packaging container.

An embodiment of this invention will be described in detail below.

An inspection method of this invention is a method for inspecting quality of a finally shaped container obtained by forming a web-like packaging laminated material having folding lines in tube shape, longitudinally sealing the packaging material in the longitudinal direction, filling foods into the tube-shaped packaging material, pressing the packaging material at every predetermined interval in the crossing direction and sealing by the transversal seal, cutting at the middle of the transversal seal zone to obtain a pillow-like preliminary forming, and sealing a flap formed by folding along the folding line to the container side wall and/or a container bottom face. One embodiment of the inspection method according to this invention comprises rotating the flap sealed to the container wall around a ridge side in which the flap integrally communicates with the container wall to peel the flap from the container wall, and returning to a shape of the pillow-like preliminary forming. Further, The embodiment according to the inspection method of this invention comprises cutting the container wall to extract the filled food, developing the cut container to prepare the sampled body, measuring an edge of the transversal seal zone on the inside of the container over the whole length of the outer surface of the edge for unevenness of the outer surface by a detecting unit, and judging acceptability of the transversal seal zone based on signals from the detecting unit by an analyzing unit.

In the inspection method according to the preferred embodiment, said detecting unit emits illumination light to the outer surface of the edge of the transversal seal zone from a plurality of directions, and said analyzing unit which is an image processing unit receives images of reflected/scattered light reflected or scattered from the outer surface of the edge to perform analysis processing.

In the inspection method according to the other preferred embodiment, said detecting unit suspends a contact element onto the outer surface of the edge on the transversal seal zone and scans over whole length of the outer surface, and said analyzing unit analyses contact degree between the outer surface of the edge and the contact element.

The embodiment of the inspection device according to this invention is a device for inspecting quality of a finally shaped container obtained by forming a web-like packaging laminated material having folding lines in tube shape, longitudinally sealing the packaging material in the longitudinal direction, filling food into the tube-shaped packaging material, pressing the packaging material at every predetermined interval in the crossing direction and sealing by the transversal seal, cutting at the middle of the transversal seal zone and obtaining a pillow-like preliminary forming, and sealing a flap formed by folding along the folding line to the container side wall and/or a container bottom face. The embodiment of the inspection device according to this invention comprises:

a pre-processing unit for rotating the flap sealed to the container wall around a ridge side in which the flap integrally communicates with the container wall to peel the flap from the container wall, and for returning to a shape of the pillow-like preliminary forming, a cutting unit for cutting the container wall to extract the filled food, a preparing unit for developing the cut container to prepare the desired sampled body, a detecting unit for measuring the edge of the transversal seal zone on the inside of the container for unevenness of the outer surface over whole length of the outer surface of the edge, and, an analyzing unit for judging acceptability of the transversal seal based on signals from the detecting unit.

In the preferred embodiment of the inspection device according to this invention, said detecting unit is illumination light emitted onto the outer surface of the edge on the transversal seal zone from a plurality of directions, and said analyzing unit is an image processing unit to receive image of reflected/scattered light reflected or scattered from the outer surface of the edge, and analyze and process.

In the preferred embodiment of the inspection device according to this invention, said detecting unit is a contact element suspended on the outer surface of the edge of the transversal seal zone and scanning over whole length of the outer surface, and said analyzing unit is a contact analyzing processing unit to analyze and process contact degree between the outer surface of the edge and the contact element.

An embodiment of this invention will be described below with reference to the drawing.

The object of the quality inspection method in this embodiment is a container obtained as shown in FIG. 1. A packaging material web 1 wound in roll-shape having a predetermined folding line is wound out. The tubular packaging material is formed by forming rollers 6. Both ends of the packaging material is lapped, and an overlap is formed. The overlap is longitudinally sealed in longitudinal line by a longitudinal seal element 8. Food is filled into the tubular packaging material from a filling pipe 7. The tube, while being sent downward by a length equivalent to one packaging container, is sandwiched by the sealing jaw 10 and the oppositely arranged jaw 11. Two transversal seal zones are formed by transversally sealing in the crossing direction. A pillow-like preliminary forming 12 is continuously formed. The middle of the seal zone of the connected pillow-like preliminary forming is cut by knife or the like. The individual pillow-like preliminary formings 13 are obtained. The upper and lower flaps of the pillow-like preliminary forming 13 separated at a final folder 15 are bent. It is formed to the finally shaped packaging filling container 14.

Figure 4:
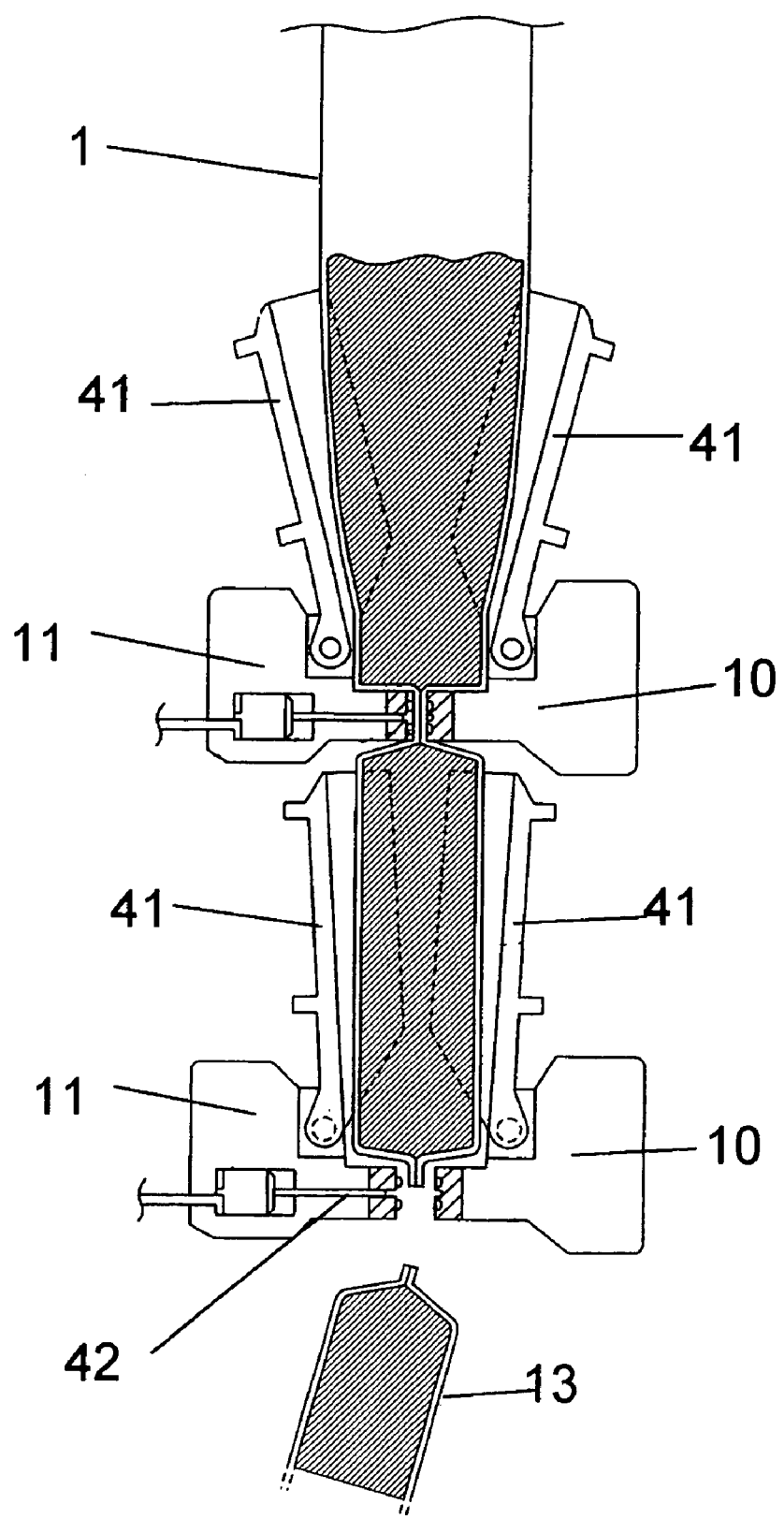
FIG. 4 is a partially sectional view of side view of transversal seal device of a packaging filling machine for paper packaging container.

FIG. 4 shows a partially cross sectional view of the detail of the transversal sealing device. In this embodiment, while the tubular packaging material 1 filled with food is being sent downward by a length equivalent to one packaging container, it is sandwiched by two pairs of forming flaps 41 and formed to rough container shape. It is sandwiched by two pairs of seal jaw 10 and oppositely arranged jaw 11, transversally sealed in the crossing direction and then two transversal seal zones are formed. The middle of the seal zone of the connected pillow-like preliminary forming is cut by knife 42, and the forming is separated to individual pillow-like preliminary forming 13.

Figure 3:
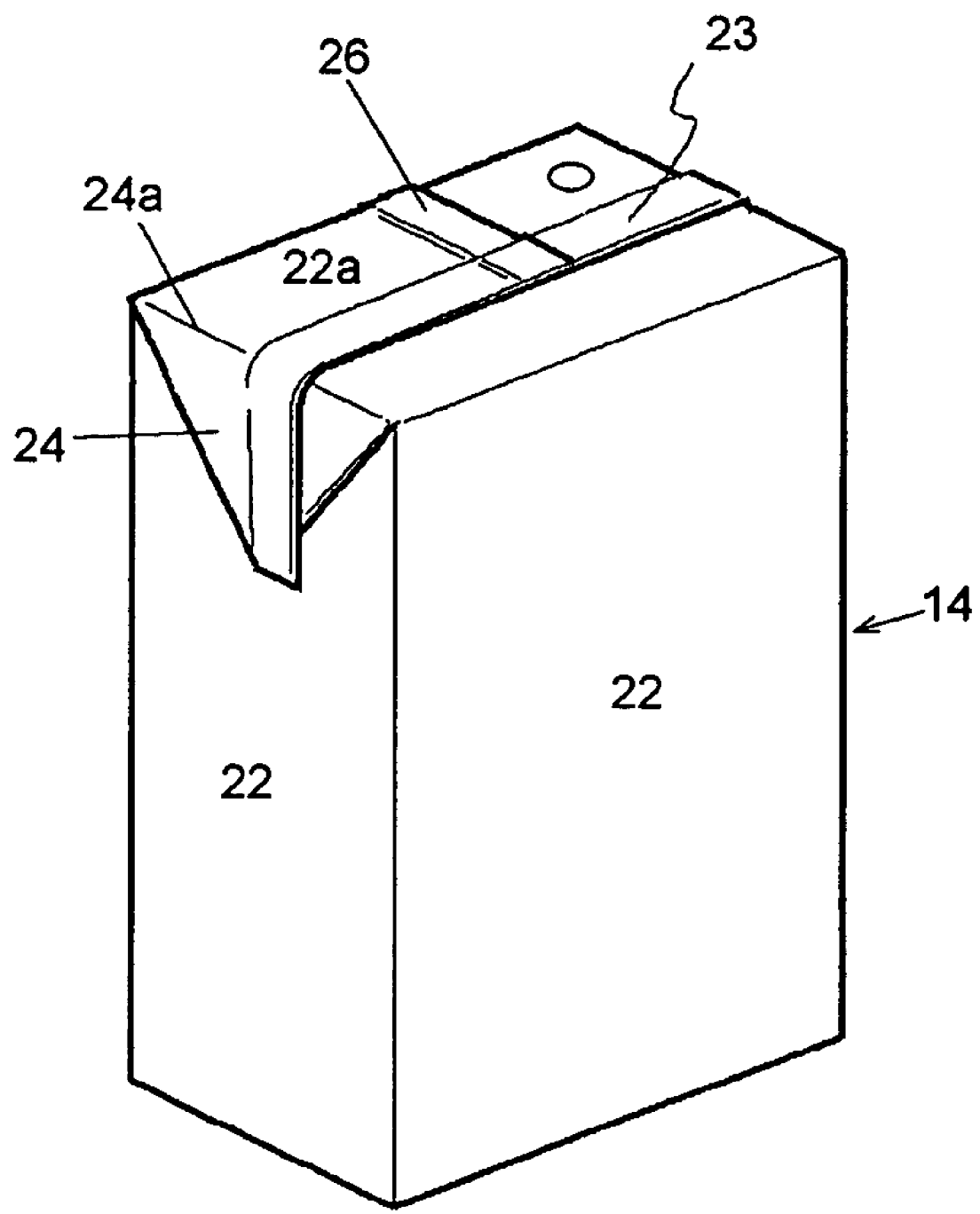
FIG. 3 is an overview of a rectangular solid paper packaging container.

The obtained container rectangular solid liquid food filling paper-made container 14 as shown in FIG. 3. The container 14 has a longitudinal seal zone 26 running to the bottom face from the folded transversal seal zone 23, container wall 22 and 22a and top wall 22a through the container wall on the back, and is provided with a flap 24 folded through a ridge side 24a.

Figure 2:
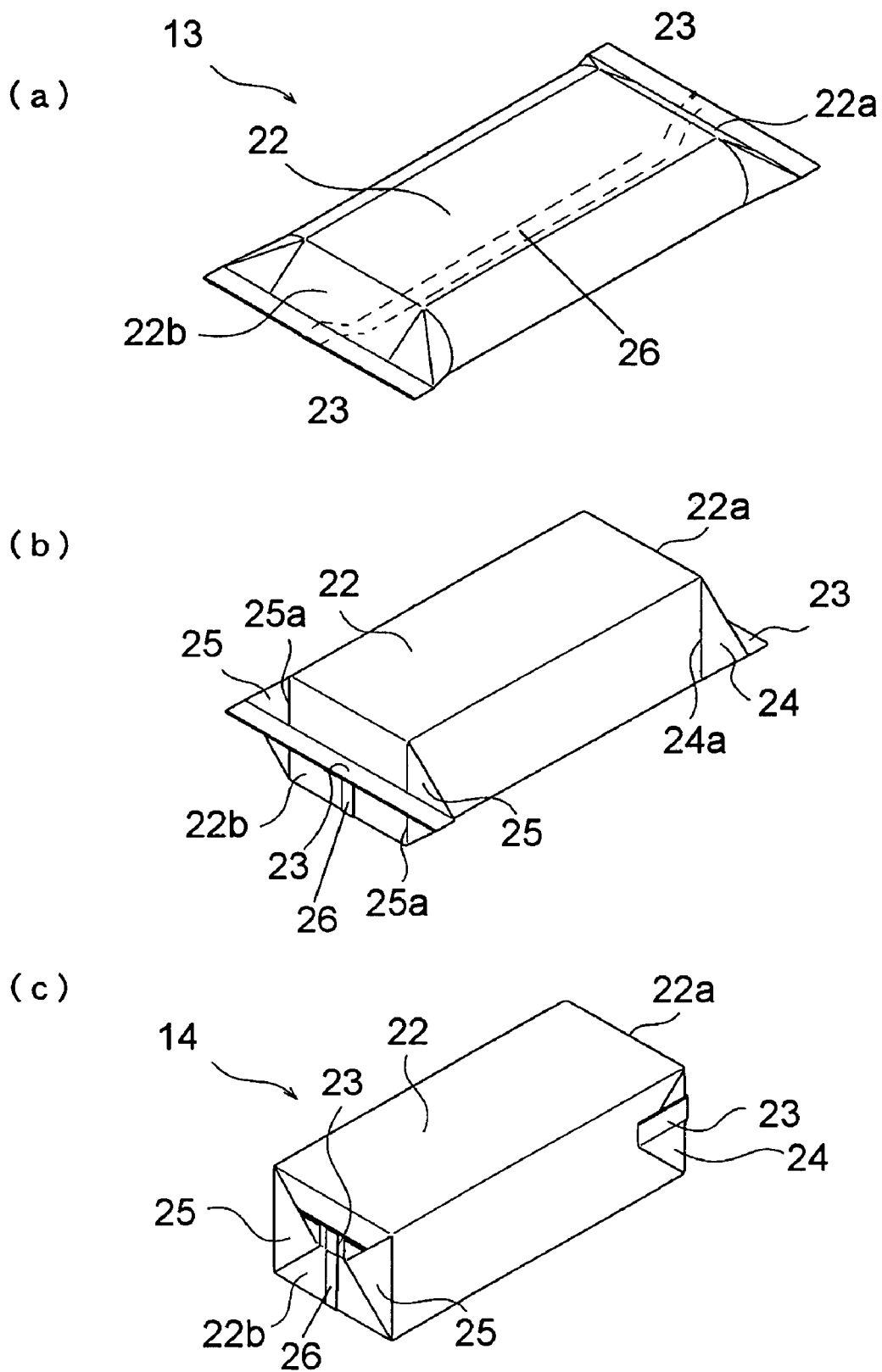
FIG. 2 is an overview explaining a configuration to form a finally shaped paper packaging container from a preliminary forming.

In the embodiment according to this invention, the above described container is returned to a shape of the pillow-like preliminary forming by rotating the flap sealed to the container wall around the ridge side where the flap integrally communicates with the container wall, and peeling from the container wall in a method substantially reverse to the method in which the flap is folded by the final folder of the filling packaging machine as shown in FIG. 2.

Figure 5:
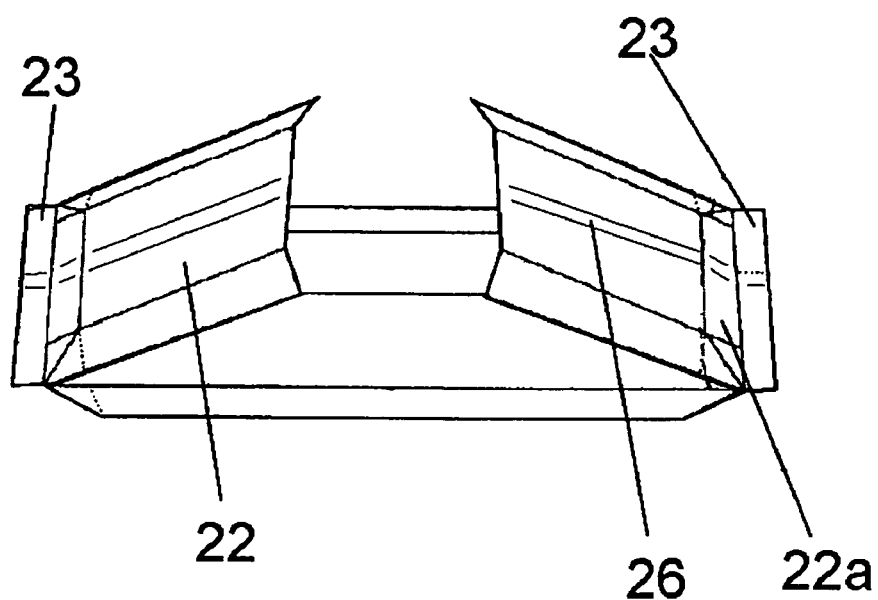
FIG. 5 is a perspective view showing preparation of a sampled body according to one embodiment of this invention.
Figure 6:
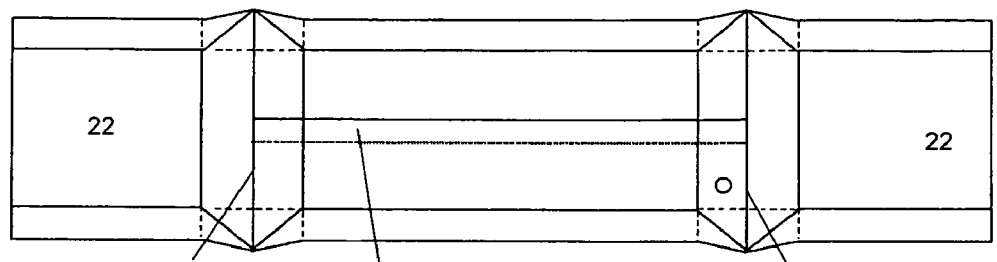
FIG. 6 is a plan and side view of a sampled body according to one embodiment of this invention.
Figure 6:
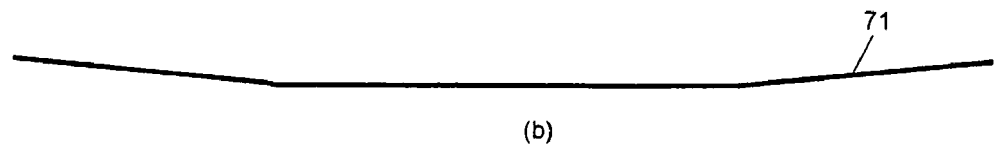

Next, the container wall is cut by a cutting unit, and the filled food is taken out, and then the pillow-like preliminary forming is changed to plate-shape. As shown in FIG. 5, the transversal side portion of the plate-shaped preliminary forming is cut, and the middle of the container wall 22 on one side is cut in the crossing direction. The cut container is substantially developed to plane-like or the predetermined shape, and then the sample body 71 as shown in FIG. 6 (*a*), (*b*) is prepared by a preparing unit.

In the embodiment of quality inspection according to this invention, the detecting unit suspends a contact element onto the outer surface of the edge on the transversal seal zone and scans over whole length of the outer surface, and the analyzing unit analyses contact degree between the outer surface of the edge and the contact element.

Figure 7:
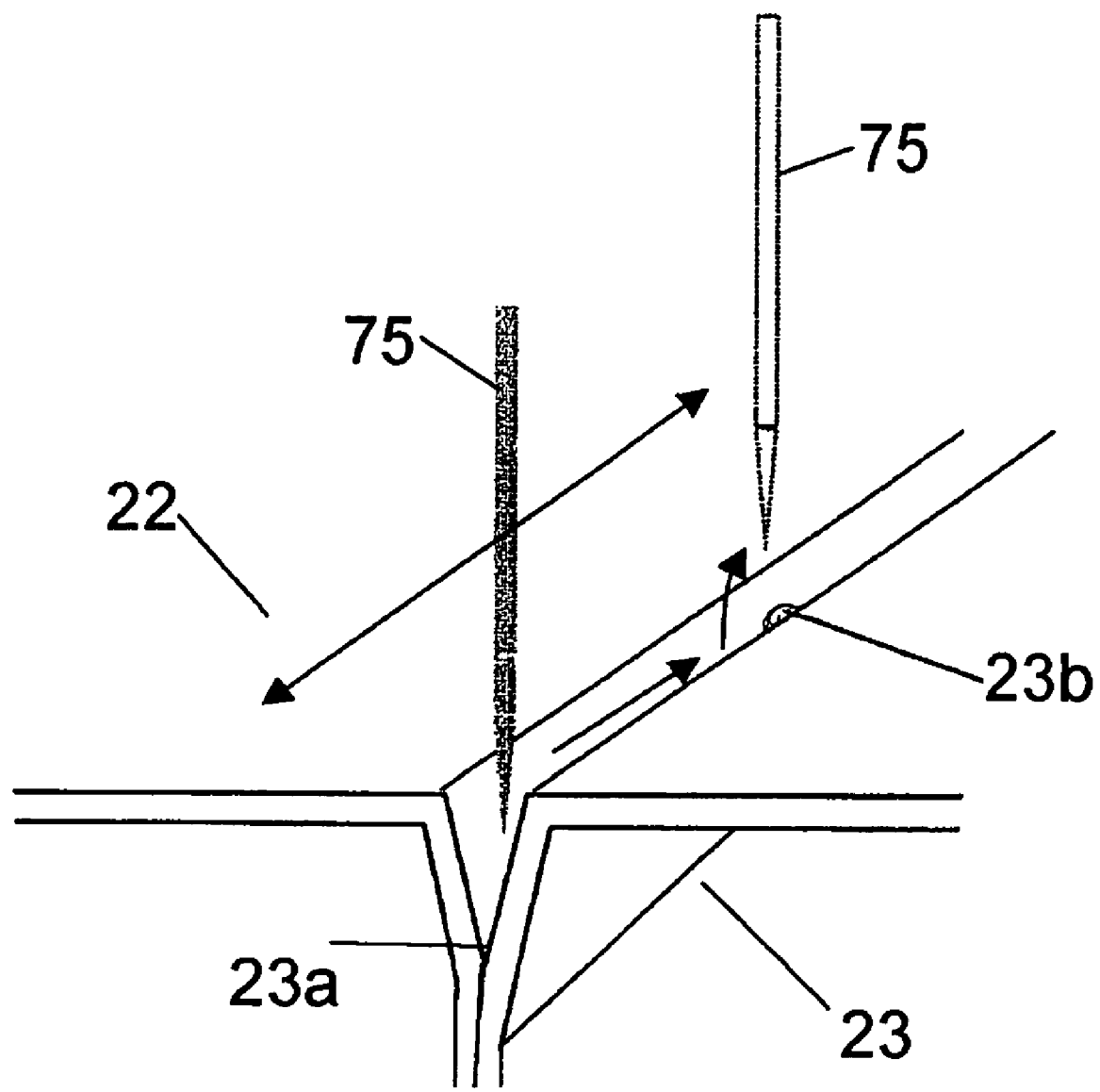
FIG. 7 is an explanatory view showing an inspection method according to one embodiment of this invention.

In this embodiment, a contact element is used for inspection for protrusion of a melted thermoplastic material of transversal line seal into inside. FIG. 7 is a perspective view showing outline of the inspection. A contact element 75 scans the edge 23a inside of the container on the transversal seal zone 23 of the sampled body 71 for which the container wall 22 is developed. That is, the contact element 75 of the detecting unit is suspended on the outer surface of the edge 23a on the transversal seal zone 23 and scans over whole length of the outer surface. If there exists protrusion 23b of a melted thermoplastic material on the transversal line seal, the contact element 75 contacts and detects. The analyzing unit (not shown) analyzes contact degree between the outer surface of the edge and the contact element.

Figure 8:
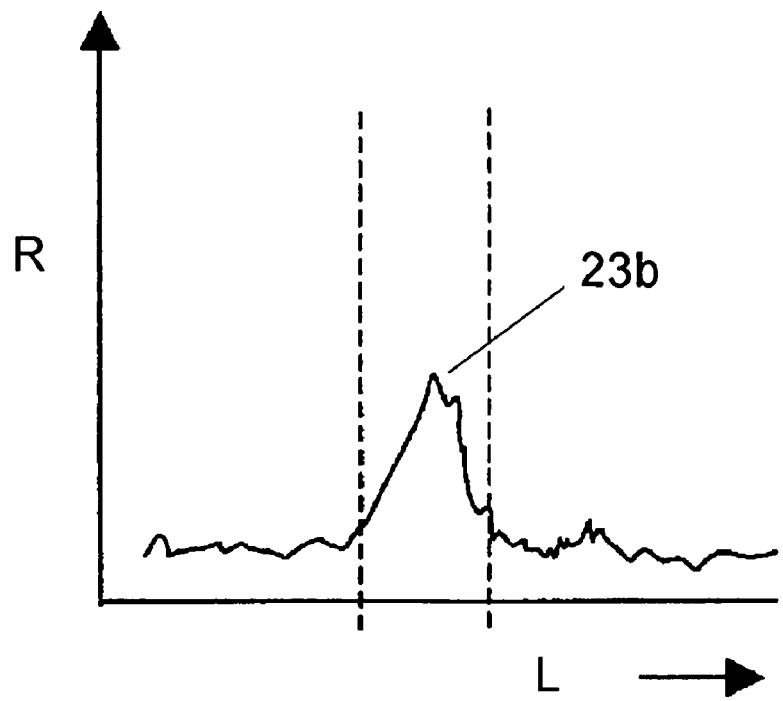
FIG. 8 is a graph showing an inspection result according to one embodiment of this invention.

FIG. 8 shows a graph of scanning distance L and resistance R of the edge 23a showing signal transmitted to the analyzing unit from the contact element 75. The existence of the protrusion 23b causes the resistance to sharply increase at the distance position, and the analyzing unit detects existence of protrusion.

In a second embodiment of the quality inspection according to this invention, light of the detecting unit emits illumination light to the outer surface of the edge of the transversal seal zone, and the analyzing unit which is an image processing unit receives images of reflected/scattered light reflected or scattered from the outer surface of the edge to perform analysis processing (image processing).

Figure 9:
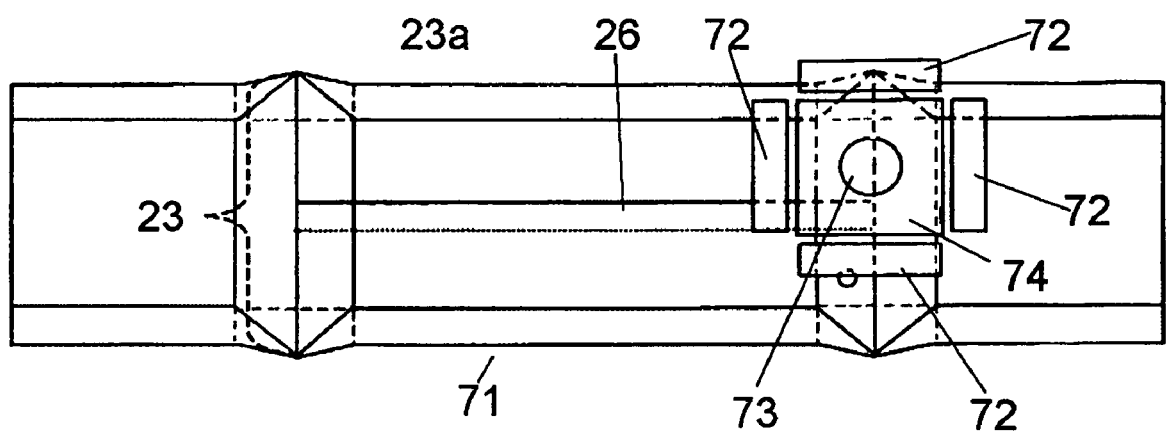
FIG. 9 is a plan view showing an inspection according to the other embodiment of this invention.
Figure 10:
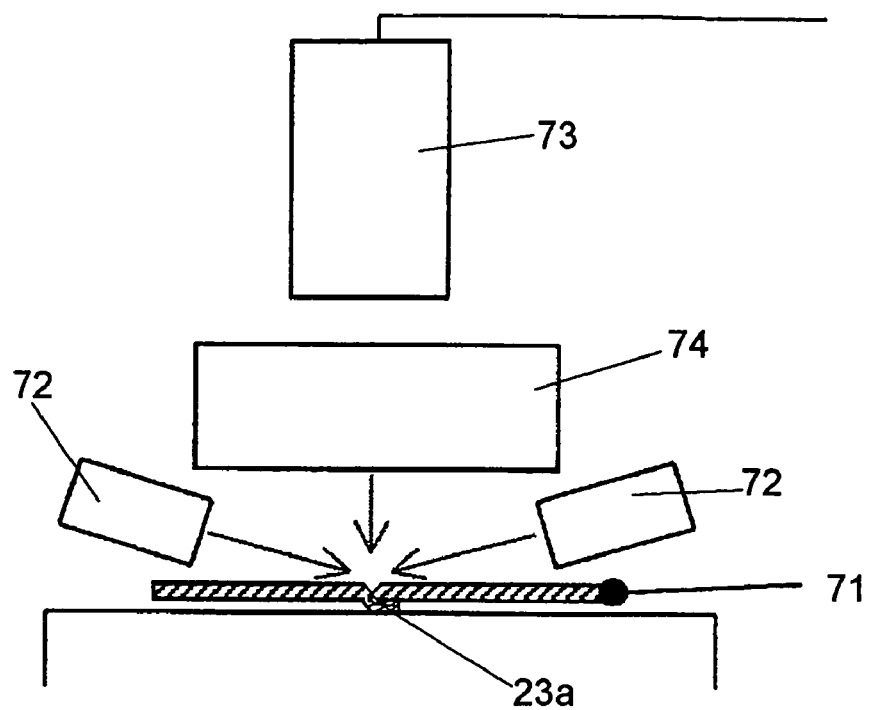
FIG. 10 is a front view showing an inspection according to the other embodiment of this invention.

FIG. 9 shows a plan view of the second quality inspection embodiment. FIG. 10 shows a front view of the second quality inspection embodiment. In this embodiment, the surface on the inside of the container on the edge 32a of the transversal seal zone 23 of the sampled body 71 is illuminated by four side lights 72 from the side, and illuminated from the upper by a upper light 74. The image processing unit (not shown) receives image of reflected/scattered light reflected or scattered from the outer surface of the edge by a CCD camera 73 and image-processes.

Figure 11:
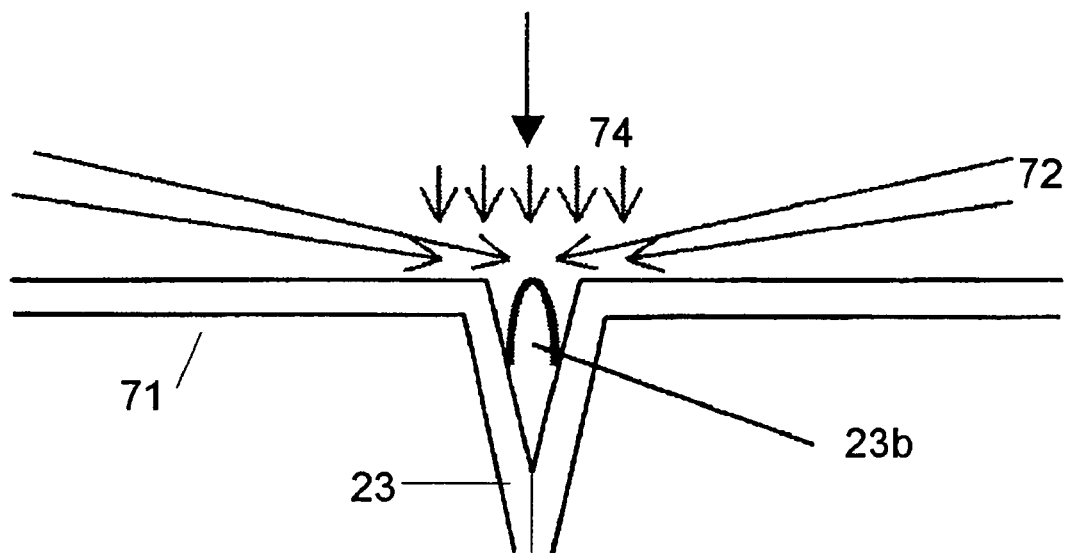
FIG. 11 is an enlarged sectional view showing an inspection according to the other embodiment of this invention.

FIG. 11 shows an en enlarged cross sectional view. The surface of the edge 32a on the transversal seal zone of the sampled body 71 is illuminated by the side light 72 from the side, and illuminated by the upper light 74 from the upper. The image processing unit receives image of reflected/scattered light scattered from the outer surface of the edge by the CCD camera 73 and image-processes.

As described above, according to this invention, the following advantageous effects can be obtained. The quality inspection according to this invention can easily detect projection on edge of seal in inspection for protrusion of the melted thermoplastic material on the transversal seal to inside.

The quality inspection according to this invention can securely capture even fine unevenness which could not be visually found. The quality inspection according to this invention allows for accurate and reliable inspection without variation of inspection.

INDUSTRIAL AVAILABILITY

The inspection method and inspection device are used to inspect quality of paper-made containers or the like filled with liquid food such as juice and milk.

What is claimed is:

1. A quality inspection method for inspecting quality of a finally shaped container obtained by forming a web-like packaging laminated material having folding lines in tube shape, longitudinally sealing the packaging material in the longitudinal direction, filling food into the tube-shaped packaging material, pressing the packaging material at every predetermined interval in the crossing direction and sealing by the transversal seal, cutting at the middle of the transversal seal zone and obtaining a pillow-like preliminary forming, and sealing a flap formed by folding along the folding line to the container side wall and/or a container bottom face, comprising:

rotating the flap sealed to the container wall around a ridge side where the flap integrally communicates with the container wall to peel the flap from the container wall;

returning to a shape of the pillow-like preliminary forming;

cutting the container wall to extract the filled food;

developing the cut container to prepare a sampled body;

measuring an edge of the transversal seal zone on the inside of the container over the whole length of the outer surface of the edge for unevenness of the outer surface by a detecting unit; and judging acceptability of the transversal seal zone based on signals from the detecting unit by an analyzing unit.

2. The quality inspection method according to claim 1, wherein said detecting unit emits illumination light to the outer surface of the edge of the transversal seal zone from a plurality of directions, and said analyzing unit which is an image processing unit receives images of reflected/scattered light reflected or scattered from the outer surface of the edge to perform analysis processing.

3. The quality inspection method according to claim 1, wherein said detecting unit suspends a contact element onto the outer surface of the edge on the transversal seal zone and scans over whole length of the outer surface, and said analyzing unit analyses contact degree between the outer surface of the edge and the contact element.

4. A quality inspection device for inspecting quality of a finally shaped container obtained by forming a web-like packaging laminated material having folding lines in tube shape, longitudinally sealing the packaging material in the longitudinal direction, filling food into the tube-shaped packaging material, pressing the packaging material at every predetermined interval in the crossing direction and sealing by the transversal seal, cutting at the middle of the transversal seal zone to obtain a pillow-like preliminary forming, and sealing a flap formed by folding along the folding line to the container side wall and/or a container bottom face, comprising:

a pre-processing unit for rotating the flap sealed to the container wall around a ridge side in which the flap integrally communicates with the container wall to peel the flap from the container wall, and for returning to a shape of the pillow-like preliminary forming;

a cutting unit for cutting the container wall to extract the filled food;

a preparing unit for developing the cut container to prepare the desired sampled body;

a detecting unit for measuring the edge of the transversal seal zone on the inside of the container for unevenness of the outer surface over whole length of the outer surface of the edge, and, an analyzing unit for judging an acceptability of the transversal seal based on signals from the detecting unit.

5. The quality inspection device according to claim 4, wherein said detecting unit is illumination light emitted onto the outer surface of the edge on the transversal seal zone from a plurality of directions, and said analyzing unit is an image processing unit to receive image of reflected/scattered light reflected or scattered from the outer surface of the edge, and analyze and process.

6. The quality inspection device for inspecting quality according to claim 4, wherein said detecting unit is a contact element suspended on the outer surface of the edge of the transversal seal zone and scanning over whole length of the outer surface, and said analyzing unit is a contact analyzing processing unit to analyze and process contact degree between the outer surface of the edge and the contact element.

* * * * *